United States Patent
Plöger et al.

(10) Patent No.: US 9,782,511 B2
(45) Date of Patent: Oct. 10, 2017

(54) BIORESORBABLE WOUND DRESSING

(71) Applicants: BIOPHARM GESELLSCHAFT ZUR BIOTECHNOLOGISCHEN ENTWICKLUNG VON PHARMAKA MBH, Heidelberg (DE); CARL FREUDENBERG KG, Weinheim (DE)

(72) Inventors: Frank Plöger, Heidelberg (DE); Denis Reibel, Herrlisheim (FR); Dirk Grafahrend, Mannheim (DE); Daniel Neumüller, Weinheim (DE)

(73) Assignees: Biopharm Gesellschaft Zur Biotechnologischen Entwicklung von Pharmaka MBH, Heidelberg (DE); Carl Freudenberg KG, Weinheim (DE)

(*) Notice: Subject to any disclaimer, the term of this patent is extended or adjusted under 35 U.S.C. 154(b) by 0 days.

(21) Appl. No.: 14/996,483

(22) Filed: Jan. 15, 2016

(65) Prior Publication Data
US 2016/0199530 A1     Jul. 14, 2016

Related U.S. Application Data

(62) Division of application No. 14/128,185, filed as application No. PCT/EP2012/061965 on Jun. 21, 2012, now Pat. No. 9,278,156.

(30) Foreign Application Priority Data

Jun. 22, 2011 (EP) .................................. 11170971

(51) Int. Cl.
| | | |
|---|---|---|
| A61K 38/00 | (2006.01) |
| A61K 38/16 | (2006.01) |
| A61K 38/17 | (2006.01) |
| A61K 38/18 | (2006.01) |
| A61L 15/32 | (2006.01) |
| A61L 15/64 | (2006.01) |
| A61F 13/00 | (2006.01) |
| A61L 15/18 | (2006.01) |
| A61L 15/22 | (2006.01) |
| A61L 15/42 | (2006.01) |
| A61L 15/44 | (2006.01) |
| A61L 15/62 | (2006.01) |
| D04H 1/30 | (2012.01) |
| D04H 1/4266 | (2012.01) |

(52) U.S. Cl.
CPC .............. *A61L 15/32* (2013.01); *A61F 13/00* (2013.01); *A61K 38/1875* (2013.01); *A61L 15/18* (2013.01); *A61L 15/22* (2013.01); *A61L 15/325* (2013.01); *A61L 15/425* (2013.01); *A61L 15/44* (2013.01); *A61L 15/62* (2013.01); *A61L 15/64* (2013.01); *D04H 1/30* (2013.01); *D04H 1/4266* (2013.01); *A61L 2300/252* (2013.01); *A61L 2300/414* (2013.01); *A61L 2300/604* (2013.01)

(58) Field of Classification Search
None
See application file for complete search history.

(56) References Cited

U.S. PATENT DOCUMENTS

| | | | |
|---|---|---|---|
| 8,871,710 B2* | 10/2014 | Pohl ..................... | C07K 14/475 424/94.1 |
| 9,278,156 B2 | 3/2016 | Plöger et al. | |
| 2005/0169965 A1 | 8/2005 | Paulista et al. | |
| 2009/0163936 A1 | 6/2009 | Yang et al. | |
| 2010/0015196 A1 | 1/2010 | Kimble et al. | |
| 2010/0021517 A1 | 1/2010 | Ahlers et al. | |
| 2010/0172952 A1 | 7/2010 | Srouji et al. | |
| 2010/0196447 A1 | 8/2010 | Kaplan et al. | |
| 2010/0285291 A1 | 11/2010 | Reibel et al. | |
| 2010/0299970 A1 | 12/2010 | Verstraelen et al. | |
| 2010/0303881 A1 | 12/2010 | Hoke et al. | |
| 2012/0165939 A1 | 6/2012 | Kladakis et al. | |
| 2013/0122066 A1* | 5/2013 | Ploeger .................. | A61L 15/44 424/400 |
| 2013/0309221 A1 | 11/2013 | Pohl et al. | |
| 2014/0141050 A1 | 5/2014 | Plöger et al. | |

FOREIGN PATENT DOCUMENTS

| | | |
|---|---|---|
| CN | 101861173 | 10/2010 |
| EP | 1462126 | 9/2004 |
| EP | 1698691 | 9/2006 |
| EP | 1872804 | 1/2008 |
| EP | 1880731 | 1/2008 |
| EP | 2042199 | 4/2009 |

(Continued)

OTHER PUBLICATIONS

Erlacher et al. (1998, J Bone Miner Res 13:383-392).*
"Tooth—American Dental Association", http://www.mouthhealthy.org/en/az-topics/t/tooth, accessed May 22, 2017.*
"Periodontium", http://www.infodentis.com/tooth-anatomy/supporting-structure-php, accessed May 33, 2017.*
"Types of Nervous Tissue", https://www.boundless.com/physiology/textbooks/boundless-anatomy-and-physiology-textbook/organization-at-the-tissue-level-4/nervous-tissue-63/types-of-nervous-tissue-1557-17319/, accessed May 22, 2017.*
Chinta et al., 2005, Int. J. Biochem. Cell Biol. 37:942-946.*
U.S. Appl. No. 14/128,185 , "Final Office Action", dated Aug. 21, 2015, 13 pages.
U.S. Appl. No. 14/128,185 , "Non-Final Office Action", dated Mar. 11, 2015, 14 pages.

(Continued)

*Primary Examiner* — Elizabeth C Kemmerer
(74) *Attorney, Agent, or Firm* — Kilpatrick Townsend & Stockton LLP

(57) ABSTRACT

The present invention is directed to novel non-woven fabrics containing growth and differentiation factor proteins. Said fabrics are specifically designed to accelerate tissue regeneration and wound healing processes of mammalian tissues. Furthermore, the invention provides wound dressings, pads or implants comprising the novel non-woven fabrics.

25 Claims, 8 Drawing Sheets
(1 of 8 Drawing Sheet(s) Filed in Color)

(56) References Cited

FOREIGN PATENT DOCUMENTS

| | | |
|---|---|---|
| JP | 08209435 | 8/1996 |
| JP | 2001505097 | 4/2001 |
| JP | 2005168646 | 6/2005 |
| JP | 2006254722 | 9/2006 |
| JP | 2007510820 | 4/2007 |
| JP | 2008055144 | 3/2008 |
| JP | 2009543566 | 12/2009 |
| JP | 2010520377 | 6/2010 |
| JP | 2010539347 | 12/2010 |
| JP | 2010539357 | 12/2010 |
| JP | 2011019923 | 2/2011 |
| JP | 2011507609 | 3/2011 |
| RU | 2005106261 | 8/2005 |
| RU | 2331411 | 8/2008 |
| RU | 2014101762 | 7/2015 |
| WO | 03060076 | 7/2003 |
| WO | 2004014304 | 2/2004 |
| WO | 2005047493 | 5/2005 |

OTHER PUBLICATIONS

U.S. Appl. No. 14/128,185 , "Notice of Allowance", dated Nov. 6, 2015, 7 pages.
Choi et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", Journal of Materials Science: Materials in Medicine, vol. 12, No. 1, Jan. 1, 2001, pp. 67-73.
Jung et al., "Local application of a collagen type I/hyaluronate matrix and growth and differentiation factor 5 influences the closure of osteochondral defects in a minipig model by enchondral ossification", Growth Factors, vol. 24, No. 4, Jan. 1, 2006, pp. 225-232.
Kim et al., "Periodontal wound healing/regeneration following implantation of recombinant human growth/differentiation factor-5 (rhGDF-5) in an absorbable collagen sponge carrier into one-wall intrabony defects in dogs: a dose-range study", Journal of Clinical Periodontology, vol. 36, No. 7, Jul. 1, 2009, pp. 589-597.
Li et al., "Electrospun silk-BMP-2 scaffolds for bone tissue engineering", Biomaterials, vol. 27, No. 16, Jun. 1, 2006, pp. 3115-3124.
Maehara et al., "Repair of large osteochondral defects in rabbits using porous hydroxyapatite/collagen (HAp/Col) and fibroblast growth factor-2 (FGF-2)", Journal of Orthopaedic Research, Jan. 1, 2009.
Min et al., "Wound healing/regeneration using recombinant human growth/differentiation factor-5 in an injectable poly-lactide-co-glycolide-acid composite carrier and a one-wall intra-bony defect model in dogs", Journal of Clinical Periodontology, vol. 38, No. 3, Mar. 1, 2011, pp. 261-268.
International Patent Application No. PCT/EP2012/061965 , "International Search Report", dated Nov. 12, 2012, 6 pages.
International Patent Application No. PCT/EP2012/061965 , "Notification of Transmittal of the International Preliminary Report on Patentability", dated Dec. 4, 2013, 20 pages.
Translation of "Decision on Grant Patent for Invention" in Russian Application No. 2014101762 ,dated Dec. 4, 2015, 5 pages.
English translation of the Office Action in Russian Patent Application No. RU 2014101762/15 (002633) dated Aug. 4, 2015, 4 pages.
Yilgor et al., "Incorporation of a sequential BMP-2/BMP-7 delivery system into chitosan-based scaffolds for bone tissue engineering", Biomaterials, vol. 30, No. 21, Jul. 2009, pp. 3551-3559.
Feng et al., "Novel PLA-PVP amphiphilic copolymers combined with recombinant bone morphogenetic protein for repairing rabbit mandibular defects", Journal of Clinical Rehabilitative Tissue Engineering Research, vol. 11, No. 35, Sep. 2007, pp. 6946-6949.
English translation of Office Action in Japanese Patent Application No. JP 2014-516347, Feb. 23, 2016, 7 pages.
Japanese Patent Application No. JP2014-516347, Office Action dated Sep. 13, 2016.
English translation of Japanese Patent Application No. JP2014-516347, Office Action dated Sep. 13, 2016.

\* cited by examiner

```
            1    mrlpklltfl    lwylawldle    fictvlgapd
lgqrpqgtrp  glakaeaker  pplarnvfrp
           61    gghsygggat    nanarakggt    gqtggltqpk
kdepkklppr  pggpepkpgh  ppqtrqatar
          121    tvtpkgqlpg    gkappkagsv    pssfllkkar
epgpprepke  pfrpppitph  eymlslyrtl
          181    sdadrkggns    svkleaglan    titsfidkgq
ddrgpvvrkq  ryvfdisale  kdgllgaelr
          241    ilrkkpsdta    kpaapgggra    aqlklsscps
grqpaslldv  rsvpgldgsg  wevfdiwklf
          301    rnfknsaqlc    leleawergr    avdlrglgfd
raarqvheka  lflvfgrtkk  rdlffneika
          361    rsgqddktvy    eylfsqrrkr    raplatrqgk
rpsknlkarc  srkalhvnfk  dmgwddwiia
          421    pleyeafhce    glcefplrsh    leptnhaviq
tlmnsmdpes  tpptccvptr  lspisilfid
          481    sannvvykqy    edmvvescqc  r
```

| Sequence | % Identity | Identical Residues |
|---|---|---|
| GDF-5 Homo | 100 | 102/102 |
| GDF-5 Mus | 99 | 101/102 |
| GDF-6 Mus | 86 | 88/102 |
| GDF-6 Homo | 85 | 87/102 |
| GDF-7 Homo | 81 | 83/102 |
| GDF-7 Mus | 80 | 82/102 |
| BMP-2A | 57 | 58/102 |
| BMP-2B | 57 | 58/102 |
| BMP-5 | 52 | 53/102 |
| BMP-9 | 51 | 52/102 |
| BMP-10 | 51 | 52/102 |
| BMP-8A | 51 | 51/102 |
| BMP-6 | 51 | 52/102 |
| BMP-7 | 51 | 52/102 |
| GDF-3 | 49 | 50/102 |
| BMP-8B | 48 | 49/102 |
| BMP-3A | 47 | 48/103 |
| GDF-9B | 45 | 46/102 |
| BMP-3B | 43 | 44/103 |
| GDF-8 | 37 | 38/103 |

Fig. 3

|  | ALP assay | | ELISA | |
| --- | --- | --- | --- | --- |
|  | biological activity [%] | mean biological activity [%] | recovery [%] | mean recovery [%] |
| before sterilization | 87.1 to 99.8 | 93±10 | 98.2 to 94.3 | 96 ±10 |
| after sterilization | 90.8 to 92.6 | 92±10 | 84.2 to 95.3 | 90 ±10 |

Fig. 8

| storage duration | storage temperature | ELISA mean recovery [%] |
|---|---|---|
| day 0 | room temperature | >90 |
| 1 day | room temperature | >90 |
| 1 day | 4 °C | >70 |
| 1 day | -80 °C | >80 |
| 3 days | room temperature | >80 |
| 3 days | 4 °C | >80 |
| 3 days | -80 °C | >90 |
| 2 weeks | room temperature | >60 |
| 2 weeks | 4 °C | >70 |
| 2 weeks | -80 °C | >60 |
| 4 weeks | room temperature | >75 |
| 4 weeks | 4 °C | >70 |
| 4 weeks | -80 °C | >70 |
| 3 months | room temperature | >90 |

Fig. 9

BIORESORBABLE WOUND DRESSING

PRIOR RELATED APPLICATIONS

This application is a Divisional Application of U.S. patent application Ser. No. 14/128,185, filed Dec. 20, 2013, now U.S. Pat. No. 9,278,156, which is a National Phase application of International Application No. PCT/EP2012/061965 filed Jun. 21, 2012, which claims priority to European Patent Application 11170971.3 filed Jun. 22, 2011. Each of the foregoing is incorporated herein by reference in its entirety.

DESCRIPTION

The present invention is directed to novel non-woven fabrics containing growth and differentiation factor proteins. Said fabrics are specifically designed to accelerate tissue regeneration and wound healing processes of mammalian tissues. Furthermore, the invention provides wound dressings, pads and implants comprising the novel non-woven fabrics.

GDF-5 (Hötten et al. 1994, Biochem. Biophys Res. Commun. 204, 646-652) is a morphogen which has been shown to promote cell proliferation, differentiation and/or tissue formation in several tissues. The protein is also known as morphogenic protein MP52, bone morphogenetic protein-14 (BMP-14) or cartilage-derived morphogenetic protein-1 (CDMP-1). GDF-5 is closely related to GDF-6 and GDF-7. These three proteins form a distinct subgroup of the TGF-β superfamily, thus displaying comparable biological properties and an extraordinary high degree of amino acid sequence identity (see i.e. Wolfman et al. 1997, J. Clin. Invest. 100, 321-330). All family members are initially synthesized as larger precursor proteins which subsequently undergo proteolytic cleavage at a cluster of basic residues approximately 110-140 amino acids from the C-terminus, thus releasing the C-terminal mature protein parts from the N-terminal prodomain. The mature polypeptides are structurally related and contain a conserved bioactive domain comprising six or seven canonical cysteine residues which is responsible for the characteristical three-dimensional "cystine-knot" motif of these proteins. Native GDF-5 related proteins are homodimeric molecules and act mainly through interaction with specific receptor complexes which are composed of type I and type II serine/threonine receptor kinases. The receptor kinases subsequently activate Smad proteins, which then propagate the signals into the nucleus to regulate target gene expression.

It has repeatedly been demonstrated that members of the GDF-5/-6/-7 subgroup are primarily important inducers and regulators of bone and cartilage (Cheng et al. 2003, J. Bone & Joint Surg. 85A, 1544-1552; Settle et al. 2003, Developm. Biol. 254, 116-130). GDF-5 is a natural growth factor in the nervous system (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). Furthermore, it is e.g. useful for the modulation of skin related tissue growth (WO 02/076494; Battaglia et al. 2002, Trans. Orthop. Res. Soc. 27, 584), and for induction of angiogenic processes (Yamashita et al. 1997, Exp. Cell Res. 235, 218-26).

After discovery of their unique tissue inductive activities, growth factor proteins such as GDF-5 have been successfully applied in therapeutic research and regenerative surgery, in which they promote and assist the natural healing process of various damaged tissues, either alone or in combination with specific matrix materials. Although several pharmaceutical compositions comprising biologically active mature GDF-5 related proteins have been developed (see e.g. WO96/33215), formulation and handling of GDF-5 are nevertheless still problematic because the mature protein tends to interact with a couple of solid materials and shows exceptional poor solubility under physiological conditions. A pH-dependent solubility profile of mature GDF-5/MP52 (shown i.e. in EP 1 462 126) reveals that the protein starts precipitating in aqueous solutions with a pH above 4.25 and becomes almost unsoluble between pH 5 and pH 9.

For wound healing purposes, both lotion-like and solid surgical dressings of various forms, sizes and materials have been developed which are primarily designed to ensure wound closure under semi-sterile conditions. Several of these dressings are made up of organic materials such as e.g. collagens whereas other devices are composed of synthetic components such as e.g. amorphous thermoplastic polymers. Some wound dressings of the most advanced generation feature additional drug delivery functions; they are capable of administering bioactive substances such as antibiotics or cytokines like epidermal growth factor (EGF) or platelet-derived growth factor (PDGF/Becaplermin). For example, genetically engineered PDGF is commercially available under the brand name Regranex® as a topical (0.01%) wound healing gel which has been approved for the treatment of diabetic foot ulcers that extend into the subcutaneous tissue or beyond.

Especially desirable for wound healing and other tissue regeneration purposes are new fabrics by which growth and differentiation factor proteins are being delivered to the human body. It is therefore an object of the present invention to improve the therapeutic usability of GDF-5 and related proteins by providing novel wound healing materials and devices.

Biodegradable wound dressings are described in EP 2 042 199. The described wound dressing is made of a non-woven fabric comprising fibres of a fibre raw material, wherein the fibres include at least one biologically active substance. As biologically active substances particularly antimicrobial substances or antibiotics are suggested.

During their studies for improving the therapeutic usability of GDF-5 and related proteins, the inventors of the present application surprisingly found out that a non-woven fabric comprising fibres of a fibre raw material as described in EP 2 042 199 is particularly suitable for delivering growth and differentiation factor proteins to the human body. The combination of GDF-5 and bioresorbable non-wovens showed unexpected effects beneficial for application of GDF-5. Biodegradable non-wovens provided a substrate for GDF-5 showing increased release of mature protein combined with good handling properties. This combination allows controlling the administration of GDF-5 in a local manner, and therefore enables the effect of the growth factor at the desired site of pharmacological action. Besides this spatial control, increased yields of bioactive GDF-5 are eluted from the biodegradable non-woven over desired time period, e.g. several days. Due to the incorporation of GDF-5 into the non-woven fabric pH dependent precipitation effects are overcome and interaction with solid materials is minimized.

Subject-matter of the invention is therefore a non-woven fabric comprising fibres of a fibre raw material comprising bioresorbable polymers, the fibres including at least one biologically active substance which is a GDF-5 related protein, distributed in the fibres.

Definitions

In order to avoid misunderstandings and ambiguities, some frequently used terms herein are defined and exemplified as follows:

The term "cystine-knot domain" as used herein means the well known and conserved cysteine-rich amino acid region which is present in the mature parts of TGF-beta superfamily proteins such as i.e. human GDF-5 and forms a three-dimensional protein structure known as cystine-knot. In this domain the respective location of the cysteine residues to each other is important and is only allowed to vary slightly in order not to lose the biological activity. It has been demonstrated that the cystine-knot domain alone is sufficient for the biological function of the protein (Schreuder et al. (2005), Biochem Biophys Res Commun. 329, 1076-86). Consensus sequences for cystine-knot domains are well known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 precursor protein (SEQ ID NO: 2) consists of the amino acids 400-501 (see also FIG. 1).

The term "GDF-5-related protein" as used herein means any naturally occurring or artificially created protein which is very closely related to human growth/differentiation factor 5 (hGDF-5). Common feature of all GFD-5-related proteins is the occurrence of a cystine-knot-domain with an amino acid identity of at least 60% to the 102 aa cystine-knot domain of human GDF-5 (amino acids 400-501 of SEQ ID NO: 2), which is sufficient for the biological function of the protein. The term "GDF-5-related proteins" includes proteins belonging to the group of GDF-5, GDF-6 and GDF-7 proteins from vertebrate or mammalian species as well as recombinant variants thereof as long as these proteins show the above mentioned percentage of identity with the cystine-knot-domain of human GDF-5. The limiting value of 60% is well suitable to separate members of the GDF-5/-6/-7 group of proteins as well as variants thereof from further proteins such as more distantly related GDFs and BMPs. A comparison of the 102 aa cystine-knot-domains of human GDF-5, human GDF-6 and human GDF-7 (see FIG. 2) reveals the high grade of amino acid identity between these proteins. Human GDF-6 shares 87 (85%) and human GDF-7 shares 83 (81%) identical residues with the cystine-knot-domain of human GDF-5. The respective domains of GDF-5/-6/-7 molecules from other vertebrate and mammalian species which have been identified so far also show very high identity percentages of at least 75% (between 79% and 99%), when compared with human GDF-5. In contrast, GDFs and BMPs not belonging to the GDF-5/-6/-7 subgroup display much lower identity values below 60% (see FIG. 3)

The determination of corresponding amino acid positions in related amino acid sequences as well as the calculation of percentages of identity can be easily performed with the help of well known alignment algorithms and optionally computer programs using these algorithms. For example, the amino acid identities in this patent application (i.e. FIG. 2) have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in Thompson, J. D., Gibson, T. J., Plewniak, F., Jeanmougin, F. and Higgins, D. G. (1997): The ClustalX windows interface: flexible strategies for multiple sequence alignment aided by quality analysis tools. Nucleic Acids Research 24:4876-4882. ClustalX is a windows interface for the ClustalW multiple sequence alignment program and is i.e. available from various sources, i.e. by anonymous ftp from ftp-igbmc.u-strasbg.fr, ftp.embl-heidelberg.de, ftp.ebi.ac.uk or via download from the following webpage: http://www-igbmc.u-strasbg.fr/BioInfo/. The ClustalW program and algorithm is also described in detail in Thompson, J. D., Higgins, D. G. and Gibson, T. J. (1994): CLUSTALW: improving the sensitivity of progressive multiple sequence alignment through sequence weighting, positions-specific gap penalties and weight matrix choice. Nucleic Acids Research 22:4673-4680.

Especially preferred GDF-5-related proteins display amino acid identities of at least 70%, 80%, 90% or 95% to the 102 aa cystine-knot domain of human GDF-5.

Non-limiting examples for vertebrate and mammalian GDF-5-related proteins are precursors and mature proteins of human GDF-5 (disclosed as MP52 in WO95/04819 and as human GDF-5 in Witten et al. 1994, Biochem. Biophys Res. Commun. 204, 646-652), recombinant human (rh) GDF-5/MP52 (WO96/33215), MP52 Arg (WO97/06254); HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol Biotechnol. 16, 203-210), chicken (*Gallus gallus*) GDF-5 (NCBI accession no. NP_989669), african clawed frog (*Xenopus laevis*) GDF-5 (NCBI accession no. AAT99303), monomeric GDF-5 (WO 01/11041 and WO 99/61611), human GDF-6/BMP-13 (U.S. Pat. No. 5,658,882), mouse GDF-6 (NCBI accession no NP_038554), GDF-6/CDMP-2 (WO96/14335), human GDF-7/BMP-12 (U.S. Pat. No. 5,658,882), mouse GDF-7 (NCBI accession no AAP97721), GDF-7/CDMP-3 (WO96/143335). Covered by the invention are also GDF-5-related proteins having additional mutations such as substitutions, additions and deletions, as long as these additional mutations do not completely abolish the biological protein activity. Some preferred variants are mutants of GDF-5-related proteins with improved biological activity. For example, one or more residues which are normally present in the human GDF-5 precursor protein (see FIG. 1) are substituted in these mutants by other amino acids: the arginine at position 438 of the human GDF-5 precursor is replaced by glycine, alanine, valine, leucine, isoleucine, methionine or asparagines; and/or serine 439 is replaced by aspartic acid, glutamic acid, glycine, leucine, or isoleucine; and/or asparagine 445 is replaced by serine or threonine. In another high activity mutant, methionine 453 and/or methionine 456 are replaced by alanine, valine, or isoleucine. Also of special interest are mutants in which leucine 441 is replaced by proline.

The term "variant" as used herein means any of the following polypeptides:
a) biologically active fragments of a protein, preferably at least comprising the cystine-knot domain;
b) biologically active protein constructs which contain additional sequences (either with or without adding biological functions) in excess to the original sequence of the protein or constructs which contain amino acid substitutions;
c) any combination of a) and b).

The term "biological activity" denotes the activity of compounds, including, e.g., a GDF-5-related protein as measured by the common in vitro alkaline phosphatase assay (ALP), e.g. as described in example 8 or in Takuwa et al. (1989), Am. J. Physiol. 257, E797-E803). Suitable cell lines which may be used in such ALP assay are e.g. ATDC-5 or MCHT 1/26 cells.

The non-woven fabric of the present invention may have different forms, shapes, styles or designs. For example, the non-woven fabric may be a wound dressing, wound pad, implant or wadding.

Subject-matter of the invention is a non-woven fabric comprising fibres of a fibre raw material comprising bioresorbable and/or biocompatible polymers, the fibres including at least one biologically active substance, wherein the biologically active substance is a GDF-5-related protein. The GDF-5-related protein is distributed in the fibres. Optionally, additional GDF-5-related protein may be present on the fibres.

The inventors surprisingly found that GDF-5 related proteins, despite their relatively high hydrophobicity, can be incorporated inside the fibres. Even non-glycosylated GDF-5 related proteins can surprisingly well be incorporated into fibres of a fibre raw material comprising bioresorbable and/or biocompatible polymers.

By the incorporation of GDF-5 related proteins into the inner part of the fibres, the stability of the protein is increased. The protein is especially protected, if the fibres are subsequently subjected to a sterilization process e.g. using γ-radiation. Due to its position in the inner part of the fibre, the protein is also protected against degradation by proteases. Further, the long-term storage ability is increased. Especially at higher temperatures as e.g. room temperature, the storage ability of the protein is improved as compared to fibres including the GDF-5 related protein on their surface. Furthermore, by selecting appropriate polymers for the raw material, the release of GDF-5 related proteins from the inner part of the fibres can be controlled, e.g. for a fast release of the active substance or a more slowly release.

According to the invention, the fibre raw materials are preferably selected from the group consisting of natural polymers, synthetic polymers and polymers derived from fossil raw materials. These materials may each be modified or unmodified.

"Natural polymers" in terms of the present invention are those which are derived from biological sources such as plant, animal, fungi or bacteria-based material. The term includes post-treated and chemically modified polymers. According to a preferred embodiment of the invention, the natural polymers are selected from the group consisting of polypeptides, polysaccharides, polyhydroxy esters and polynucleotides.

Particularly suitable are natural polymers as the polypeptides like collagen, gelatin, fibrin, casein, or the polysaccharides dextran, cellulose, starch, chitin, chitosan, hyaluronic acid and alginate as well as synthetic polymers as polylactide (PLA), polyglycolide (PGA), polycaprolactone (PCL), as well as any combinations thereof.

According to a preferred embodiment of the invention, the non-woven fabric is "bioresorbable". This means that the non-woven fabric is degraded in or on the body. Such materials preferably do not have to be removed after complete resorption and often are particularly well compatible with the body.

"Biocompatible" materials in terms of the present invention are materials which are able to perform with an appropriate host response in a specific application. Such materials preferably elicit little or no immune response in a given organism, or may be able to integrate with a particular cell type or tissue.

In a further preferred embodiment, the non-woven fabric is bioresorbable or/and biocompatible.

Biodegradable or bioresorbable polymers are for example alginates from algae, natural polysaccharides like dextran, polymer starch and cellulose from plants, animal polymers like collagen, gelatin, chitin, casein, polydepsipeptides, bacterial polymers like polyhydroxy ester, particularly polyhydroxybutyrates and -valerates, synthetic polymers based on plant oils as for example polylactic acid, polyglycol acid, polyamide and polyurethane, well as polymers of fossil raw materials like poly-□-caprolactone, polyvinyl alcohol, polyester, polyethylene succinate and -oxalate, polyesteramide, and polydioxanone.

Additionally insoluble substances can be dispersed into the polymer matrix. Especially inorganic substances such as hydroxylapatite or/and b-tricalcium phosphate particles showed to be suitable for this purpose.

The fabrics according to the invention are non-woven materials. These are preferably not compressed.

The diameter of the fibres can be established in a narrow distribution by means of a rotational spin method as described in EP 2 042 199. Fibres having a diameter of on average 0.1-500 μm, preferably from 3-300 μm and even more preferably from 5-100 μm can be produced, which fibres form a partial network with one another. The narrow distribution of the diameter of the fibres permits a homogeneous and stable structure of the non-woven fabric without expensive additional bonding measures and at the same time allows the controlled release of a bioactive substance like GDF-5 (which is homogenously distributed on or inside the fibres).

Some fibres could be twisted or interlaced with one another or could have a twisted structure. The twistings or interlacings additionally promote the strength and the stretching behaviour of the non-woven fabric.

Some fibres could be interlaced with one another and could form one or more fibre bundles. Through the interlacings of individual fibres, these are combined into fibre bundles and could be reversibly displaced relative to one another. As a result of this, it is possible to stretch the non-woven fabric without destruction. Due to the stretching the individual fibres are in fact pulled and are displaced relative to other fibres. The twistings and interlacings even promote the return of the fibres to their position prior to stretching. The non-woven fabric therefore shows high dimensional stability even in the wet state.

The fabrics could be modified, either by chemical means, radiation or physical treatments such as dehydrothermal treatments (DHT), in order to alter fabric characteristics. Such a modification could involve crosslinking of the fibres or polymer in order to control fabric features such as stability, degradation or bioresorption.

The GDF-5-related protein may be homogeneously distributed in the fibres. As a result of this, a gradual release of the GDF-5-related protein with a long-lasting effect can be established.

The GDF-5-related protein may be present in the fibres at the nanoscale level. Nanoscale structures are understood as meaning regions of any morphology which have dimensions in the nanometer range, at least in one direction in space. As a result of this, the GDF-5-related protein acquires high mobility. A GDF-5-related protein present at the nanoscale level shows particularly high reactivity. Furthermore, the non-woven fabric releases the GDF-5-protein very easily to media which come into contact with it. To this extent, the non-woven fabric is distinguished by a high-release capacity with respect to the GDF-5-related protein.

According to another embodiment of the invention, additional GDF-5-related protein may be distributed on the fibres. This permits spraying of a non-woven fabric with the GDF-5-related protein in order to ensure fast release to the human body. It is particularly preferred that the GDF-5-related protein is present both in and on the fibres.

In a preferred embodiment of the present invention, the GDF-5-related protein is incorporated into the non-woven fabric in combination with suitable carriers, stabilizers or further supplements as described herein below.

At least a part of the fibres may be in the form of nanofibres. A non-woven fabric of this form can be made particularly light and thin.

The non-woven fabric may have an open pore structure having an air permeability between 0.01 and 100 l/min×cm$^2$ this parameter being determined according to DIN 9237. Such a non-woven fabric is particularly suitable as dressing material since it enables the skin to release moisture and to breathe.

The production of the inventive non-woven fabric is preferably effected according to a rotational spin method as described for example in EP 2 042 199. For the execution of the rotational spin method, a device or a container is preferably used as described in German Patent Application DE 102 005 048 939.

The non-woven fabrics of the invention including a GDF-5-related protein are particularly suitable for use in the medical sector since they are very readily modifiable with regard to the fabric structure and material composition. Thus, another embodiment of the present invention is a non-woven fabric, preferably a wound dressing, wound pad or implant comprising a non-woven fabric according to the invention.

In general, the fabric of the present invention can be applied in all situations in which storage and/or delivery of the above mentioned recombinant and wild-type GDF-5 forms in combination with devices made of a non-woven fabric comprising fibres of a fibre raw material comprising bioresorbable polymers are useful. Thus, the present invention can be used to facilitate the regeneration of various tissues and organs. For example, GDF-5 is considered to be a very effective promoter of bone and cartilage formation as well as connective tissue formation (see for example WO 95/04819, Witten et al. 1996, Growth Factors 13, 65-74; Storm et al. 1994, Nature 368, 639-643; Chang et al. 1994, J. Biol. Chem. 269, 28227-28234) and formation of connective tissue attachment (EP 0 831 884). In this context, GDF-5 is useful for applications concerning the joints between skeletal elements (see for example Storm & Kingsley 1996, Development 122, 3969-3979). One example for connective tissue is tendon and ligament (Wolfman et al. 1997, J. Clin. Invest. 100, 321-330; Aspenberg & Forslund 1999, Acta Orthop Scand 70, 51-54; WO 95/16035). The protein is helpful for meniscus and spinal/intervertebral disk repair (Walsh et al. 2004, Spine 29, 156-63) and spinal fusion applications (Spiro et al. 2000, Biochem Soc Trans. 28, 362-368). GDF-5 can be beneficially applied in tooth (dental and periodontal) applications (see for example WO 95/04819; WO 93/16099; Morotome et al. 1998, Biochem Biophys Res Comm 244, 85-90) such as the regeneration of dentin or periodontal ligament. GDF-5 is also useful in wound repair of any kind. It is also beneficial for promoting tissue growth in the neuronal system and survival of e.g. dopaminergic neurons. In this context, GDF-5 can be used for treating neurodegenerative disorders like e.g. Parkinson's disease and possibly also Alzheimer's disease or Huntington chorea tissues (see for example WO 97/03188; Krieglstein et al., (1995) J. Neurosci Res. 42, 724-732; Sullivan et al., (1997) Neurosci Lett 233, 73-76; Sullivan et al. (1998), Eur. J. Neurosci 10, 3681-3688). GDF-5 allows to maintain nervous function or to retain nervous function in already damaged tissues. GDF-5 is therefore considered to be a generally applicable neurotrophic factor. It is also useful for diseases of the eye, in particular retina, cornea and optic nerve (see for example WO 97/03188; You et al. (1999), Invest Opthalmol V is Sci 40, 296-311), for hair growth and the treatment and diagnosis of skin related disorders (WO 02/076494; Battaglia et al. 2002, Trans. Orthop. Res. Soc. 27, 584), and for induction of angiogenesis (Yamashita et al. 1997, Exp. Cell Res. 235, 218-26).

As such, a preferred indication in which the present invention can be applied is wound healing. The invention is especially suited to facilitate the treatment of burns, skin lesions, skin injuries or skin grafts, diabetic wounds and diabetic ulcers, e. g. diabetic foot ulcer.

Further non-limiting examples in which the present invention can be applied are the prevention or therapy of diseases associated with bone and/or cartilage damage or affecting bone and/or cartilage disease, or generally situations, in which cartilage and/or bone formation is desirable or for spinal fusion, prevention or therapy of damaged or diseased tissue associated with connective tissue including tendon and/or ligament, periodontal or dental tissue including dental implants, neural tissue including CNS tissue and neuropathological situations, tissue of the sensory system, liver, pancreas, cardiac, blood vessel, renal, uterine and thyroid tissue, mucous membranes, endothelium, epithelium, for promotion or induction of nerve growth, tissue regeneration, angiogenesis, induction of proliferation of progenitor cells and/or bone marrow cells, for maintenance of a state of proliferation or differentiation for treatment or preservation of tissue or cells for organ or tissue transplantation, for integrity of gastrointestinal lining, for treatment of disturbances in fertility, contraception or pregnancy. Diseases concerning sensory organs like the eye are also to be included in the preferred indication of the pharmaceutical composition according to the invention. As neuronal diseases again Parkinson's and Alzheimer's diseases can be mentioned as examples.

The biological activities of GDF-5-related proteins can be easily determined with the help of established test systems. Most useful and preferred is a common in vitro test known as alkaline phosphatase (ALP) assay (Takuwa et al. 1989, Am. J. Physiol. 257, E797-E803). GDF-5-related proteins have been demonstrated to increase alkaline phosphatase activity i.e. in ROB-C26 cells (Yamaguchi et al. 1991, Calcif. Tissue Int. 49, 221-225) as described in WO95/04819, in embryonic ATDC5 cells (Riken Gene Bank, ROB 0565), in mouse stromal MCHT-1/26 cells, and in HPDL cells as shown in Nakamura et al. 2003, J. Periodontal Res. 38, 597-605.

The concentrations of GDF-5-related proteins in the compositions of the invention should be chosen in dependency on the mode and period of application. Basically, GDF-5-related proteins are highly potent cytokines which are capable of eliciting effects even in exiguous quantities. As easily determinable with the help of different biological assay systems such as i.e. the alkaline phosphatase assay described herein, a concentration of 0.1 pg GDF-5 per ml of the respective solution is sufficient to cause biological actions. Accordingly, low concentrations, i.e. ranging from 0.1 µg/ml to 1 ng/ml or less, are preferred if the compositions of the invention are repeatedly administered. However, maximum effects are achievable with higher growth factor concentrations of 1-100 ng/ml. An independent dose response analysis of GDF-5 action utilizing a wide range of serial dilutions (0.3-80 ng/ml, Farkas et al. 1997, Neurosci. Lett. 236, 120-122) gave optimal results at a concentration of 20 ng GDF-5 per ml. In vivo skin models commonly use high doses of 1-10 µg/ml. Therefore, in a preferred embodiment of the invention, the compositions of the invention contain GDF-5 related proteins in concentrations of between 0.1 µg/ml and 10 µg/ml. Preferred total doses of GDF-5 related proteins in case of one time administrations range from 10 ng to 10 µg.

A further aspect of the invention relates to additional ingredients and components disclosed herein.

In addition, the fabrics might comprise natural and synthethic lipids. All kinds of natural and synthetic oils/lipids can be used as long as they are biocompatible, for example synthetic oils or saturated esters such as ethyl palmitate, isopropyl palmitate, alkyl myristates such as those of isopropyl, butyl and cetyl, hexyl stearate, triglycerides (i.e. of octanoic or decanoic acids, medium chained tryglycerides such as Miglyol® 812), cetyl ricinoleate, stearyl octanoate (purcelllin oil) and hydrogenated polyisobutene, or natural oils such as e.g. cottonseed, soybean, sesame, sunflower, safflower, olive, avocado, peanut, walnut, almond and hazelnut oil.

The fabrics might also comprise emulsifying agents, for example phospholipids such as phosphatidylserine, phosphatidylcholine or phosphatidylethanolamine, distilled monoglycerides, mono- & diglycerides, acetic acid esters of monoglycerides, organic esters of monoglycerides, sorbitan esters of fatty acids, propylene glycol esters of fatty acids and polyglycerol esters of fatty acids.

Other bioactive protein(s) in addition to GDF-5-related proteins might also be part of the fabrics of the invention. It has been shown that TGF-β increases the size of regenerated dermis and stabilizes the dermoepithelial junction (Fitzpatrick and Rosen, J. Cosmet. Laser Ther, 5: 25-34 (2003)). A cocktail (TNS Recovery Complex, SkinMedica, Inc. Carlsbad, Calif., USA) containing seven cytokines (VEGF, IL-6 and -8, HGF, PDGF-a, GCSF, and TGF-β1) derived from neonatal foreskin fibroblasts was tested in a multicenter study. Evaluation showed improvement in skin texture, and decreased wrinkling (Rokhsar, C. K. et al., Dermatol. Surg. 31: 1166-1178 (2005)). Recombinant epidermal growth factor (ReVive Skincare); and N-furfuryladenine (kinetin) plant growth factor are also on the market. All these proteins may be used together with the GDF-5-related proteins of the invention. Other proteins which act synergistically if combined with GDF-5-related proteins are disclosed in the literature/patents, i.e. in WO 99/15191. Preferred are neurotrophins, hedgehog proteins and proteins of the transforming growth factor family, including but not limited to TGF-alpha's, TGF-beta's, activins, BMP's and GDF's. Especially preferred is a combination with any one of EGF, TGF-β1, TGF-β2, TGF-β3, NGF and/or GDNF.

Other acceptable components in the fabrics are:

Retinoids (vitamin A derivatives) which preserve the integrity of mucosal/epithelial surfaces;

Hydroxy acids (organic carboxylic acids further classified into alpha hydroxy acids (AHA) and beta hydroxyl acid (BHA)) which enhance epidermal shedding, i.e. glycolic acid, lactic acid, citric acid, mandelic acid, malic acid, and tartaric acid;

Antioxidants which counteract the harmful effects of free radicals, i.e. vitamin C, vitamin E, panthenol, lipoic acid, ubiquinone, niacinamide, dimethylaminoethanol, spin traps, melatonin, catalase, glutathione, superoxide dismutase, peroxidase, glucpyranosides, polyphenols, cysteine, allantoin, furfuryladenine, uric acid, and carnosine;

Depigmenting agents which alleviate hyperpigmentation, i.e. N-acetyl-4-S-cysteanimylphenol, kojic acid, arbutin, azaleic acid, paper-mulberry compound, chemical peeling agents (resorcinol, salicylic acid), Kligman's formula, Pathak's formula, and Westerhof's formula;

Botanicals, i.e. chamomile, ginseng, Gingko biloba, curcumin, glycyrrhizin, capsaicin, and aloe vera;

Glycosaminoglycans which support epidermal regeneration, i.e. hyaluronic acid;

Anticellulites which mediate lipolysis, i.e. beta-adrenergic stimulators such as theobromine, theophylline, aminophylline, caffeine, epinephrine and alpha1-adrenergic stimulators such as yohimbine, piperoxane, and phentolamine;

Hormones, i.e. estrogens, progesterone, testosterone, and growth hormone;

Antimicrobial agents, i.e. triclosan, chlorhexidine, povidone iodine, hydrogen peroxide, antidandruff preparations, zinc pyrithione;

Chemical UV filters, i.e. 3-benzylidene camphor (3-BC) or 4-methylbenzylidene camphor (4-MBC);

Furthermore buffers, stabilizers, preservatives, reducing agents, anti-oxidant chelating agents, agents that modify isotonicity, deodorants, anaesthetics, adjuvants and solubility-enhancing additives.

These are only non-limiting examples of possible additives, and a worker skilled in the art may easily add other excipients which are currently in use which are generally regarded as safe. For more information about methods for formulating a pharmaceutical composition and selection of pharmaceutically acceptable substances please see i.e. Remington's Pharmaceutical Sciences (luth ed.; Mack Publishing Company, Eaton, Pa., 1990), Wang et al. (1980), J. Parent. Drug Assn. 34 (6): 452-462 (1980); Wang et al. (1988), J. Parent. Sci. and Tech. 42: 4-26; Lachman et al. (1968), Drug and Cosmetic Industry 102(1): 36-38, 40 and 146-148; and Akers (1988) J. Parent. Sci. and Tech. 36 (5): 222-228. Preferably between 1% and 100% of the biologically active substance is eluted from the non-woven fabric during 3 to 7 days in contact with body fluids, plasma, media or buffer solution. Most preferably between 10% and 100% of the bioactive substance are released under physiological conditions (PBS buffer, 10% Fetal Calf Serum, 37° C.).

The following figures, examples and sequence protocols are intended to further illustrate the invention.

SEQ ID NO: 1 shows the DNA sequence, and SEQ ID NO: 2 shows the protein sequence of the human GDF-5 precursor.

SEQ ID NO: 3 shows the DNA sequence and SEQ ID NO: 4 shows the protein sequence of the human mature monomeric GDF-5.

BRIEF DESCRIPTION OF THE DRAWINGS

The file of this application or patent contains at least one drawing executed in color. Copies of this patent with color drawings will be provided by the Patent and Trademark Office upon request and payment of the necessary fee.

FIG. 1 shows additional features of the human GDF-5 precursor protein according to SEQ ID NO:2:

aa 001-381 pre-prodomain (bold letters)
aa 001-027 signal peptide (bold and underlined)
aa 382-501 mature protein part
aa 400-501 cystine-knot-domain (underlined)

Figure 2:
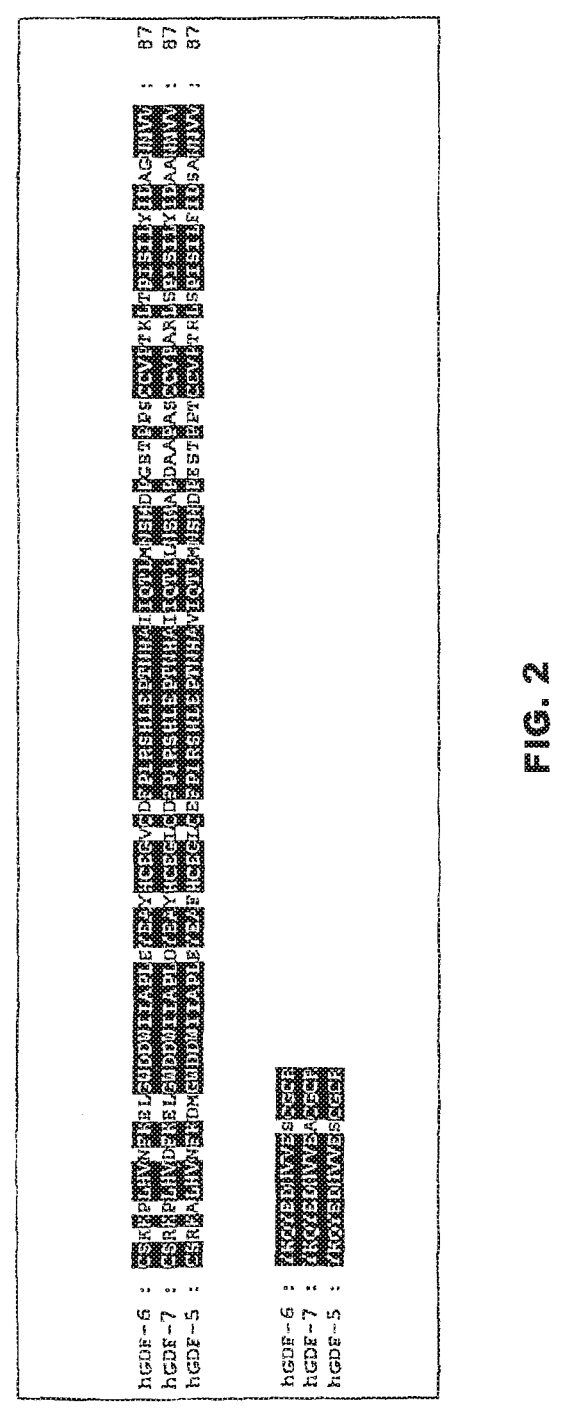

FIG. 2 shows a comparison of the 102 aa cystine-knot domains of human GDF-5 (SEQ ID NO:2), human GDF-6 (sequence 26 from U.S. Pat. No. 5,658,882) and human GDF-7 (sequence 2 from U.S. Pat. No. 5,658,882). Amino acid residues which are identical in all three molecules are highlighted by borders.

FIG. 3 shows a table with the sequence identities of cystine-knot domains of several known BMPs and GDFs to the cystine-knot-domain of human GDF-5.

Figure 4:
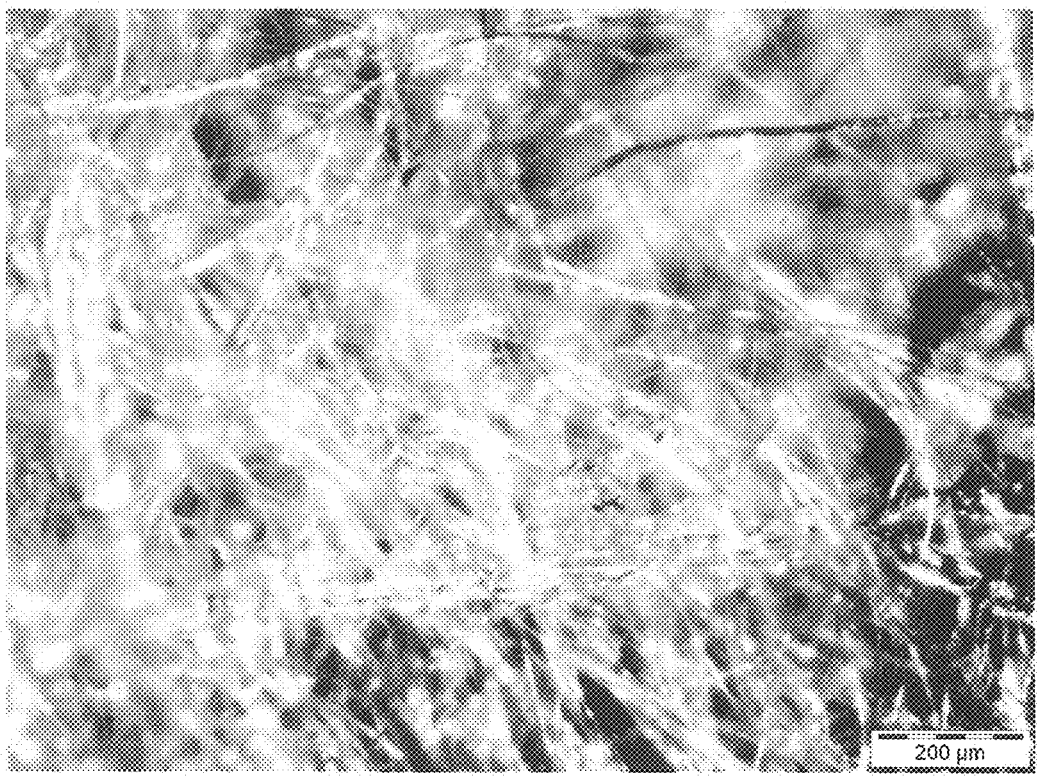

FIG. 4 shows a microscope image of a gamma sterilized gelatin/hyaluronic acid non-woven with rhGDF-5 (scale bar 200 μm).

Figure 5:
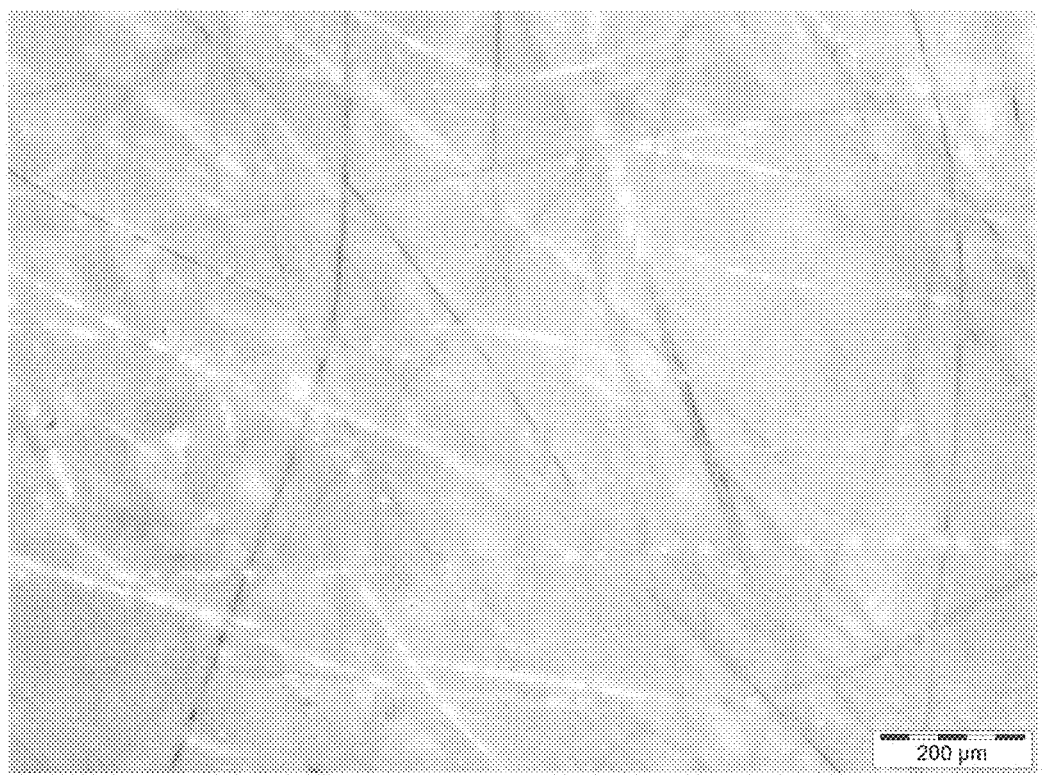

FIG. 5: shows a microscope image of a gamma sterilized gelatin/hydroxylapatie non-woven (scale bar 200 μm).

Figure 6:
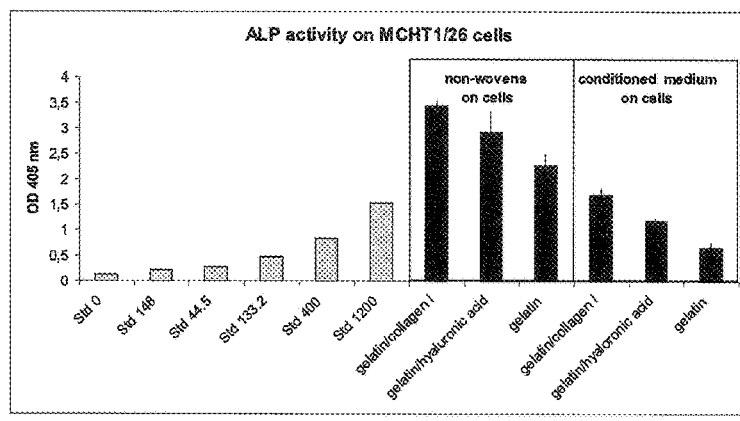

FIG. 6 shows the biological activity of GDF-5 released from fast release non-woven materials gelatin, gelatin/hyaluronic acid and gelatin/collagen I. Biological activity of GDF-5 was measured using an alkaline phosphatase activity assay on mouse stromal MCHT1/26 cells as described in example 1. MCHT1/26 cells were stimulated with 4.8-1200 ng/ml of GDF-5 dissolved in 10 mM HCl (standard curve).

The GDF-5 release from the non-woven materials were analysed by placing the non-wovens directly on MCHT1/26 cells and in parallel with conditioned medium, produced by GDF-5 release in cell culture medium for 3 days at 37° C. ALP activity was measured by the conversion of p-nitrophenolphosphate to p-nitrophenolate at 405 nM. The data are average values of three independent measurements.

The attached table shows the calculated concentrations of released GDF-5 (ng/ml) from the corresponding non-wovens and the GDF-5 recovery given in %. For the calculation it was assumed, that 2 μg GDF-5 coated on non-wovens were completely released in 160 μl cell culture medium, this corresponds to a GDF-5 concentration of 12500 ng/ml (100% release value for the assay with non-wovens directly tested on the cells). In case of the quantification of the conditioned medium on the cells, 40 μl release cell culture medium corresponds to a GDF-5 concentration of 2500 ng/ml (100% release value for the assay with conditioned cell culture medium tested on the cells).

Figure 7:
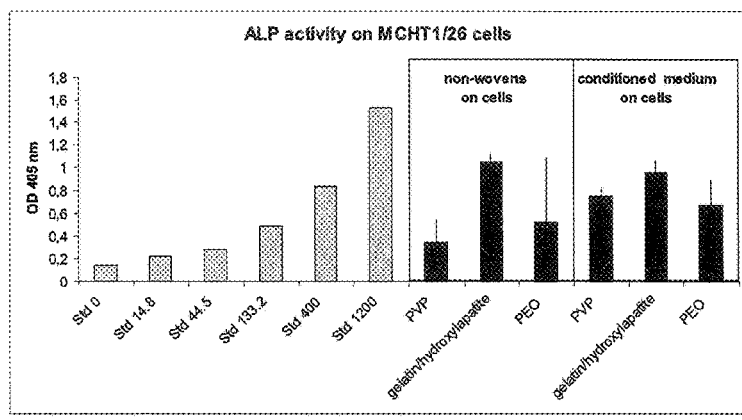

FIG. 7 shows the biological activity of GDF-5 released from slow release non-woven materials polyvinylpyrrolidone, polyethylene oxide and gelatin/hydroxylapatite. Biological activity of GDF-5 was measured using an alkaline phosphatase activity assay on mouse stromal MCHT1/26 cells as described in example 1. MCHT1/26 cells were stimulated with 4.8-1200 ng/ml of GDF-5 dissolved in 10 mM HCl (standard curve).

The GDF-5 release from the non-woven materials were analysed by placing the non-wovens directly on MCHT1/26 cells and in parallel with conditioned medium, produced by GDF-5 release in cell culture medium for 3 days at 37° C. ALP activity was measured by the conversion of p-nitrophenolphosphate to p-nitrophenolate at 405 nM. The data are average values of three independent measurements.

The attached table shows the calculated concentrations of released GDF-5 (ng/ml) from the corresponding non-wovens and the GDF-5 recovery given in %. For the calculation it was assumed, that 2 μg GDF-5 were completely released from the non-woven in 160 μl cell culture medium, this corresponds to a GDF-5 concentration of 12500 ng/ml (100% release value for the assay with non-wovens directly tested on the cells). In case of the quantification of the conditioned medium on the cells, 40 μl release cell culture medium corresponds to a GDF-5 concentration of 2500 ng/ml (100% release value for the assay with conditioned cell culture medium tested on the cells).

FIG. 8 shows the biological activity and recovery of GDF-5 released from non-woven materials before and after sterilization by gamma irradiation. Biological activity was measured using an alkaline phosphatase activity assay on mouse stromal MCHT1/26 cells. The recovery of released GDF-5 from non-wovens was quantified by GDF-5 specific sandwich ELISA. The GDF-5 release from the non-woven materials were analysed by placing non-wovens in cell culture medium for 24 hours at 37° C. An equal amount of GDF-5 without non-woven material was incubated in cell culture medium under identical conditions and served as positive control. ALP activity was measured by the conversion of p-nitrophenolphosphate to p-nitrophenolate at 405 nm. The data are average values of at least three independent measurements. For the ELISA, recovery of GDF-5 was quantified by the amount of bound strepatavidin-horseradish-peroxidase to the biotinylated secondary antibody. Detection was carried out by enzymatic conversion of the substrate tetramethylbenzidine dihydrochloride, followed by photometry at 450 nm.

The table shows the calculated biological activity, measured by ALP activity assay, given in % (the OD value of the positive control was set to 100%). For the ELISA data, the table shows the GDF-5 recovery from the non-woven material given in %. For the calculation it was assumed that, that 200 ng GDF-5 incorporated into the non-woven material were completely released in 200 μl cell culture medium, this corresponds to a GDF-5 concentration of 1000 ng/ml (100% value).

FIG. 9 shows the results of a stability study of sterilized GDF-5 incorporated into non-wovens stored at room temperature, 4° C., and −80° C. for a time period of 1 day up to 3 month. Day 0 is starting point of the stability study. The stability of GDF-5 was investigated by measuring the recovery of GDF-5 released from sterilized non-wovens by GDF-5 specific sandwich ELISA. The GDF-5 release from the non-woven materials was analysed by placing non-wovens in cell culture medium for 24 hours at 37° C. A defined amount of release medium was transferred to the ELSIA system, where the recovery of GDF-5 was quantified by the amount of bound strepatavidin-horseradish-peroxidase to the biotinylated secondary antibody. Detection was carried out by enzymatic conversion of the substrate tetramethylbenzidine dihydrochloride, followed by photometry at 450 nm. The table shows the GDF-5 recovery from non-woven material given in %, calculated from released GDF-5.

EXAMPLES

Example 1: Non-Wovens Showing Fast GDF-5 Release Profile

Non-wovens showing fast GDF-5 release consisting of pure gelatin, gelatin and hyaluronic acid, or gelatin and collagen I, were produced as follows:

A 22.5% (w/w) aqueous solution of type A PIGSKIN gelatin (Gelita A G, Eberbach, Germany) was prepared by mixing gelatin and water. This mixture was kept for one hour at room temperature in order to swell. Thereafter, the gelatin solution was treated for one hour with ultrasonic at 60° C. and heated to 80° C. The solution remained at 80° C. for 2 hours and again was cooled to 60° C. Dependent on the desired non-woven composition, 12.5% (weight per weight gelatin) hyaluronic acid (cristalhyal, Soliance, France) or collagen I gel (DM04, Devro Medical, Australia) were mixed into the solution and stirred with a spatula for one minute in order to dissolve or disperse. The gelatin based solution was fed by a syringe pump into the spinning device described in DE 10 2005 048 939 A.

In the case of incorporation of the growth factor into the filaments, GDF-5 solution (1200 μg/ml 5 mM sodium acetate buffer) was mixed into the solution directly before entering the container of the spinning device. The container was heated to 50° C. and rotated at 3500 rpm. Due to centripetal force the liquid material was ejected as liquid jets from the orifices and fibres were formed. These fibres were stretched by a suction mechanism underneath the container of the spinning device and collected as non-woven. The non-wovens were collected and punched to the final sample size (3×3 mm). Non-woven samples showing fast GDF-5 releases were obtained, which afterwards were gamma sterilized (irradiation dose 25 kGy).

The GDF-5 release from the non-woven samples was measured using a GDF-5 sensitive alkaline phosphatase (ALP) activity assay on mouse stromal MCHT1/26 cells (Hoechst Japan Ltd., Kawagoe, Japan). The release properties and cell compatibility of the non-woven materials were tested a) directly on the cells and b) with conditioned medium. For the production of conditioned medium, non-woven samples were incubated for three days at 37° C., 5% $CO_2$ in 200 μl cell culture medium (alpha-MEM supplemented by 2 mM L-glutamine and 10% fetal calf serum) without cells. After the incubation period the conditioned medium and the non-woven samples were analyzed on MCHT1/26 cells.

MCHT1/26 cells were plated at $4.5 \times 10^3$ cells per well in 96-multiwell plates in cell culture medium (alpha-MEM, (Sigma, Taufkirchen, Germany) supplemented by 2 mM L-glutamine, (Invitrogen, Karlsruhe, Germany) and 10% fetal calf serum (Invitrogen, Karlsruhe, Germany). After 24 h, cells were incubated with 40 μl conditioned release medium supplemented with 120 μl fresh cell culture medium. In parallel non-woven samples were placed directly on cells with 160 μl cell culture medium. After 72 h, cells were washed with phosphate buffered saline (PBS) and extracted with alkaline phosphate buffer 1, containing 1% Nonidet P40, 0.1 M glycine pH 9.6 (Sigma, Taufkirchen, Germany), 1 mM $MgCl_2$ and 1 mM $ZnCl_2$ (Merck, Darmstadt, Germany). To achieve thorough cell lysis, cells were incubated 15-18 h at 37° C. Alkaline phosphatase enzyme activity was assayed with 10 mM p-nitrophenylphosphate (Pierce, Bonn, Germany) as a substrate in 0.1 M glycine pH 9.6, 1 mM $MgCl_2$ and 1 mM $ZnCl_2$. After 30 min incubation at 37° C., the absorbance was measured with an automatic microplate reader (Tecan Spectra Rainbow, TECAN, Crailsheim, Germany) at 405 nM under consideration of blank value subtraction. The results are shown in FIG. 6.

All non-woven samples were well tolerated by the marker cell line MCHT1/26. Non-wovens with GDF-5 showed fast release with gelatin material, of 22% when non-woven samples were directly placed on cells and 10% for conditioned medium. For the non-woven combination gelatin/hyaluronic acid GDF-5 release directly on the cells was 36%, with conditioned medium the release was 32%. For the non-woven combination gelatin/collagen I, GDF-5 release directly on the cells was 54%, with conditioned medium the release was 55%.

Such samples showing fast GDF-5 release may be used for wound healing, neuroprotection and angiogenesis, as high doses of the active growth factor are released into the wound environment during the first three days.

Example 2: Non-Wovens Showing Slow GDF-5 Release Profile

Non-wovens showing a slow GDF-5 release consisting of polyvinylpyrrolidone (A.), polyethylene oxide (B.) or gelatin and hydroxylapatite (C.) were produced as follows.

Firstly, the liquid precursor solutions were prepared.

A.) 40 g polyvinylpyrrolidone (Kollidon F 90, BASF AG., Germany) were filled into a beaker and a magnetic stirrer and 160 g water added. Thereafter, the mixture was stirred at room temperature for 24 h and heated to 80° C. Finally the solution was treated for one hour with ultrasonic before it was cooled back to 60° C.

B.) 15 g polyethylene oxide (molecular weight 1000 kDa, BASF AG., Germany) was dissolved in 185 g water at room temperature and heated to 60° C.

C.) A 22.5% (w/w) aqueous solution of type A PIGSKIN gelatin was prepared by mixing gelatin and water. This mixture is kept for one hour at room temperature in order to swell. Thereafter, the gelatin solution was treated for one hour with ultrasonic at 60° C. 2.5% hydroxylapatite nanoparticles (product number 677418, Sigma-Aldrich Chemie GmbH, Germany) (weight per weight gelatin) were mixed into the solution using a spatula. Afterwards, the mixture was heated to 80° C. and remained for 2 hours at this temperature before it was again cooled to 60° C.

The solutions or dispersions were fed by a syringe pump into the spinning device described in DE 10 2005 048 939 A. In the case of incorporation of the growth factor into the filaments, GDF-5 solution (1200 μg/ml 5 mM sodium acetate buffer) was mixed into the solution directly before entering the container of the spinning device. The container was heated to 60° C. and rotated at 4500 rpm. Due to centripetal force the liquid material was ejected as liquid jets from the orifices and fibres are formed. These fibres were stretched by a suction mechanism underneath the container of the spinning device and collected as non-woven. The non-wovens were collected and punched to the size of 3×3 mm. Non-woven samples showing slow GDF-5 releases were obtained, which afterwards were gamma sterilized (irradiation dose 25 kGy).

The measuring of non-woven samples with GDF-5 was performed as described in example 1. The GDF-5 release from the non-woven samples was measured using an alkaline phosphatase activity assay on mouse stromal MCHT1/26 cells. The release properties and cell compatibility of the non-woven prototypes were tested a) directly on the cells and b) with conditioned medium. The results for the slow release non-woven samples polyvinylpyrrolidone, polyethylene oxide and gelatin/hydroxylapatite are shown in FIG. 7.

Non-wovens with GDF-5 showed slow release with polyvinylpyrrolidone (PVP) of 1% when non-woven samples were directly placed on cells and 12% for conditioned medium. For the non-woven material polyethylene oxide (PEO) GDF-5 release directly on the cells was 1%, with conditioned medium the release was 6%. For the non-woven combination gelatin/hydroxylapatite, GDF-5 release directly on the cells was 5%, with conditioned medium the release was 19%.

Such samples showing slow GDF-5 release may be used for bone or cartilage regeneration as only small amounts of the active growth factor are released during the first three days.

Example 3: Non-Woven Technology Protects Incorporated GDF-5 from Destabilizing Sterilization Conditions The influence of sterilization on the stability of incorporated GDF-5 into non-woven material was investigated. Therefore, the recovery and the biological activity of GDF-5 incorporated in non-wovens were tested before and after the sterilization process. For this purpose, non-wovens with incorporated GDF-5 were produced as described in example 1. In brief, a GDF-5 solution of 200 µg/ml 5 mM sodium acetate buffer was mixed into a gelatine/collagen I mixture, giving non-wovens of 200 ng GDF-5/3×3 mm. The non-wovens were punched to a sample size of 3×3 mm and were gamma sterilized (irradiation dose 25 kGy).

The recovery of released GDF-5 from the non-wovens was quantified by ELISA and the biological activity of GDF-5 was by measured by the induction of alkaline phosphatase (ALP activity assay).

The measurement of the GDF-5 bioactivity of the non-sterilized and sterilized non-wovens, using the ALP assay is described in example 1. The amount of GDF-5 released from non-wovens before and after sterilization was performed as follows: Non-wovens with incorporated GDF-5 were incubated for 24 hours at 37° C., 5% $CO_2$ in 200 µl cell culture medium (alpha-MEM supplemented by 2 mM L-glutamine and 10% fetal calf serum). As a positive control, 200 ng GDF-5 without non-woven material were incubated under identical conditions. After the incubation period the release medium and the positive control were diluted 1:2500 and 1:4000 and were transferred to a GDF-5 specific sandwich ELISA (Biopharm, Heidelberg, Germany) The ELISA is based on two monoclonal antibodies to GDF-5. The enzyme streptavidin-horseradish-peroxidase was bound to the biotinylated secondary antibody. Detection was carried out by enzymatic conversion of the substrate tetramethylbenzidine dihydrochloride, which was determined by photometry at 450 nm. The release samples with GDF-5 and the positive control were quantified by using a test series of GDF-5 standards ranging from 50 to 500 pg/mL. The results are shown in FIG. 8.

After gamma sterilization (irradiation dose 25 kGy) of non-wovens with incorporated GDF-5 more than 95% of GDF-5 was biological active, demonstrated by ALP activity assay on MCHT1/26 cells. Furthermore, the recovery of incorporated GDF-5 from non-woven material after sterilization was 95%, quantified by GDF-5 specific ELISA method.

Example 4: GDF-5 Incorporated in Non-Wovens Shows Long Term Stability at Low and High Storage Temperatures The influence of storage duration and storage temperature on the stability of incorporated GDF-5 into non-woven material was investigated. Non-wovens with incorporated GDF-5 were stored at room temperature, 4° C., and −80° C. for a time period up to 3 months.

In order to test the stability of GDF-5 incorporated in non-wovens, non-woven samples were prepared on day 0 and were stored at room temperature, 4° C., and −80° C. After a storage period of 1 day, 3 days, 2 weeks, 4 weeks and 3 months the samples of the respective temperature conditions were analysed for stability by ELISA method.

The non-wovens with incorporated GDF-5 were produced as described in example 1. In brief, a GDF-5 solution of 200 µg/ml 5 mM sodium acetate buffer was mixed into a gelatin/collagen I mixture, giving non-wovens of 200 ng GDF-5/3×3 mm. The non-wovens were punched to a sample size of 3×3 mm and were gamma sterilized (irradiation dose 25 kGy). The stability of GDF-5 was analysed by measuring the recovery of released active GDF-5 from the non-wovens into cell culture medium. Non-wovens with incorporated GDF-5 were incubated for 24 hours at 37° C., 5% $CO_2$ in 200 µl cell culture medium (alpha-MEM supplemented by 2 mM L-glutamine and 10% fetal calf serum). After the incubation period the release medium was diluted 1:2500 and 1:4000 and was transferred to a GDF-5 specific sandwich ELISA (Biopharm, Heidelberg, Germany). The release samples with GDF-5 were quantified by using a test series of GDF-5 standards ranging from 50 to 500 µg/ml. The results for the ELISA are shown in FIG. 9.

The recovery of GDF-5 from sterilized non-wovens on day 0 (starting point of the stability study) was greater 90%. The stability of GDF-5 incorporated in non-wovens was almost identical for the investigated temperature conditions (room temperature, 4° C. and −80° C.). After a storage period of 3 months at room temperature no loss of stability could be observed.

---

The invention claimed is:

1. A method of facilitating healing of a damaged mammalian tissue, comprising applying to the damaged mammalian tissue a non-woven fabric,
wherein the non-woven fabric comprises fibres of a fibre raw material comprising bioresorbable and/or biocompatible polymers, the fibres including at least one biologically active substance, which is distributed in the fibres,
wherein the biologically active substance is a GDF-5-related protein,
wherein the GDF-5-related protein comprises a cystine-knot-domain with an amino acid identity of at least 60% to the 102 aa-cystine-knot-domain of human GDF-5 according to amino acids 400-501 of SEQ ID NO:2, and
wherein the GDF-5-related protein which is distributed in the fibres is added to the fibre raw material before forming of the fibres,
and wherein the damaged mammalian tissue is a bone tissue, a cartilage tissue, a skin tissue or a connective tissue.

2. The method of claim 1, wherein the GDF-5-related protein is additionally distributed on the fibres.

3. The method of claim 1, wherein the fibre raw material is selected from the group consisting of natural polymers, synthetic polymers, polymers derived from fossil raw materials, each of which may be modified or unmodified, and combinations thereof.

4. The method of claim 1, the non-woven fabric comprising another substance dispersed into the fibres.

5. The method of claim 1, wherein the non-woven fabric is produced by a rotation spinning method.

6. The method of claim 1, wherein at least some of the fibres are nanofibres.

7. The method of claim 1, wherein at least 10% of the biologically active substance is eluted from the non-woven fabric within 3 to 7 days after application of the non-woven fabric to the damaged mammalian tissue.

8. The method of claim 1, wherein the mammalian tissue is located in or on a body of a mammal.

9. The method of claim 1, wherein the non-woven fabric is or is a part of a wound dressing, a wound pad, a wadding or an implant.

10. A method of promoting cell proliferation or differentiation in a mammalian tissue or a mammalian organ, comprising contacting the mammalian tissue or the mammalian organ with a non-woven fabric,
wherein the non-woven fabric comprises fibres of a fibre raw material comprising bioresorbable and/or biocompatible polymers, the fibres including at least one biologically active substance, which is distributed in the fibres,
wherein the biologically active substance is a GDF-5-related protein,
wherein the GDF-5-related protein comprises a cystine-knot-domain with an amino acid identity of at least 60% to the 102 aa-cystine-knot-domain of human GDF-5 according to amino acids 400-501 of SEQ ID NO:2, and
wherein the GDF-5-related protein which is distributed in the fibres is added to the fibre raw material before forming of the fibres,
and wherein the mammalian tissue or the mammalian organ comprises a bone tissue, a cartilage tissue, a skin tissue, a connective tissue or dopaminergic neurons.

11. The method of claim 10, wherein the mammalian tissue or the mammalian organ is located in a body of a mammal.

12. The method of claim 10, wherein the mammalian tissue or the mammalian organ is a transplant.

13. The method of claim 10, wherein the GDF-5-related protein is additionally distributed on the fibres.

14. The method of claim 10, wherein the fibre raw material is selected from the group consisting of natural polymers, synthetic polymers, polymers derived from fossil raw materials, each of which may be modified or unmodified, and combinations thereof.

15. The method of claim 10, the non-woven fabric comprising another substance dispersed into the fibres.

16. The method of claim 10, wherein the non-woven fabric is produced by a rotation spinning method.

17. The method of claim 10, wherein at least some of the fibres are nanofibres.

18. The method of claim 10, wherein at least 10% of the biologically active substance is eluted from the non-woven fabric within 3 to 7 days after application of the non-woven fabric to the damaged mammalian tissue.

19. A method of healing a wound in a mammal, comprising applying to the wound a non-woven fabric,
wherein the non-woven fabric comprises fibres of a fibre raw material comprising bioresorbable and/or biocompatible polymers, the fibres including at least one biologically active substance, which is distributed in the fibres,
wherein the biologically active substance is a GDF-5-related protein,
wherein the GDF-5-related protein comprises a cystine-knot-domain with an amino acid identity of at least 60% to the 102 aa-cystine-knot-domain of human GDF-5 according to amino acids 400-501 of SEQ ID NO:2, and
wherein the GDF-5-related protein which is distributed in the fibres is added to the fibre raw material before forming of the fibres,
and wherein the healing of the wound comprises healing of a skin tissue.

20. The method of claim 19, wherein the wound is a surgical wound, a burn, an injury, a graft wound, a diabetic wound or a diabetic ulcer.

21. The method of claim 1, wherein the damaged mammalian tissue is associated with one or more of tendon, ligament, spine, spinal/intervertebral disk, or joint.

22. The method of claim 1, wherein the damaged mammalian tissue is the skin tissue or the bone tissue.

23. The method of claim 10, wherein the mammalian tissue is associated with one or more of tendon, ligament, spine, spinal/intervertebral disk, or joint.

24. The method of claim 10, wherein the mammalian organ is or is associated with tendon, ligament, spine, spinal/intervertebral disk, or joint.

25. The method of claim 10, wherein the mammalian tissue is the skin tissue or the bone tissue.

* * * * *

SEQUENCE LISTING

```
<160> NUMBER OF SEQ ID NOS: 6

<210> SEQ ID NO 1
<211> LENGTH: 2703
<212> TYPE: DNA
<213> ORGANISM: homo sapiens
<220> FEATURE:
<221> NAME/KEY: CDS
<222> LOCATION: (640)..(2142)
<223> OTHER INFORMATION: GDF-5 precursor

<400> SEQUENCE: 1
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta    240
```

-continued

```
gggggaaaaa aaaactggag cacacaggca gcattacgcc attcttcctt cttggaaaaa      300
tccctcagcc ttatacaagc ctccttcaag ccctcagtca gttgtgcagg agaaaggggg      360
cggttggctt tctcctttca agaacgagtt attttcagct gctgactgga gacggtgcac      420
gtctggatac gagagcattt ccactatggg actggataca aacacacacc cggcagactt      480
caagagtctc agactgagga gaaagccttt ccttctgctg ctactgctgc tgccgctgct      540
tttgaaagtc cactcctttc atggtttttc ctgccaaacc agaggcacct ttgctgctgc      600
cgctgttctc tttggtgtca ttcagcggct ggccagagg atg aga ctc ccc aaa        654
                                             Met Arg Leu Pro Lys
                                               1               5
```

| | |
|---|---|
| ctc ctc act ttc ttg ctt tgg tac ctg gct tgg ctg gac ctg gaa ttc<br>Leu Leu Thr Phe Leu Leu Trp Tyr Leu Ala Trp Leu Asp Leu Glu Phe<br>                  10                  15                20 | 702 |
| atc tgc act gtg ttg ggt gcc cct gac ttg ggc cag aga ccc cag ggg<br>Ile Cys Thr Val Leu Gly Ala Pro Asp Leu Gly Gln Arg Pro Gln Gly<br>          25                  30                  35 | 750 |
| acc agg cca gga ttg gcc aaa gca gag gcc aag gag agg ccc ccc ctg<br>Thr Arg Pro Gly Leu Ala Lys Ala Glu Ala Lys Glu Arg Pro Pro Leu<br>        40                  45                  50 | 798 |
| gcc cgg aac gtc ttc agg cca ggg ggt cac agc tat ggt ggg ggg gcc<br>Ala Arg Asn Val Phe Arg Pro Gly Gly His Ser Tyr Gly Gly Gly Ala<br> 55                  60                  65 | 846 |
| acc aat gcc aat gcc agg gca aag gga ggc acc ggg cag aca gga ggc<br>Thr Asn Ala Asn Ala Arg Ala Lys Gly Gly Thr Gly Gln Thr Gly Gly<br>70                75                  80                  85 | 894 |
| ctg aca cag ccc aag aag gat gaa ccc aaa aag ctg ccc ccc aga ccg<br>Leu Thr Gln Pro Lys Lys Asp Glu Pro Lys Lys Leu Pro Pro Arg Pro<br>                90                  95                100 | 942 |
| ggc ggc cct gaa ccc aag cca gga cac cct ccc caa aca agg cag gct<br>Gly Gly Pro Glu Pro Lys Pro Gly His Pro Pro Gln Thr Arg Gln Ala<br>                105                 110              115 | 990 |
| aca gcc cgg act gtg acc cca aaa gga cag ctt ccc gga ggc aag gca<br>Thr Ala Arg Thr Val Thr Pro Lys Gly Gln Leu Pro Gly Gly Lys Ala<br>        120                  125                  130 | 1038 |
| ccc cca aaa gca gga tct gtc ccc agc tcc ttc ctg ctg aag aag gcc<br>Pro Pro Lys Ala Gly Ser Val Pro Ser Ser Phe Leu Leu Lys Lys Ala<br>        135                  140                  145 | 1086 |
| agg gag ccc ggg ccc cca cga gag ccc aag gag ccg ttt cgc cca ccc<br>Arg Glu Pro Gly Pro Pro Arg Glu Pro Lys Glu Pro Phe Arg Pro Pro<br>150                 155                 160                  165 | 1134 |
| ccc atc aca ccc cac gag tac atg ctc tcg ctg tac agg acg ctg tcc<br>Pro Ile Thr Pro His Glu Tyr Met Leu Ser Leu Tyr Arg Thr Leu Ser<br>              170                 175                180 | 1182 |
| gat gct gac aga aag gga ggc aac agc agc gtg aag ttg gag gct ggc<br>Asp Ala Asp Arg Lys Gly Gly Asn Ser Ser Val Lys Leu Glu Ala Gly<br>        185                  190                  195 | 1230 |
| ctg gcc aac acc atc acc agc ttt att gac aaa ggg caa gat gac cga<br>Leu Ala Asn Thr Ile Thr Ser Phe Ile Asp Lys Gly Gln Asp Asp Arg<br>200                 205                 210 | 1278 |
| ggt ccc gtg gtc agg aag cag agg tac gtg ttt gac att agt gcc ctg<br>Gly Pro Val Val Arg Lys Gln Arg Tyr Val Phe Asp Ile Ser Ala Leu<br>        215                  220                  225 | 1326 |
| gag aag gat ggg ctg ctg ggg gcc gag ctg cgg atc ttg cgg aag aag<br>Glu Lys Asp Gly Leu Leu Gly Ala Glu Leu Arg Ile Leu Arg Lys Lys<br>230                 235                 240                  245 | 1374 |
| ccc tcg gac acg gcc aag cca gcg gcc ccc gga ggc ggg cgg gct gcc<br>Pro Ser Asp Thr Ala Lys Pro Ala Ala Pro Gly Gly Gly Arg Ala Ala<br>        250                  255                  260 | 1422 |

```
cag ctg aag ctg tcc agc tgc ccc agc ggc cgg cag ccg gcc tcc ttg          1470
Gln Leu Lys Leu Ser Ser Cys Pro Ser Gly Arg Gln Pro Ala Ser Leu
            265                 270                 275 ctg gat gtg cgc tcc gtg cca ggc ctg gac gga tct ggc tgg gag gtg          1518
Leu Asp Val Arg Ser Val Pro Gly Leu Asp Gly Ser Gly Trp Glu Val
        280                 285                 290 ttc gac atc tgg aag ctc ttc cga aac ttt aag aac tcg gcc cag ctg          1566
Phe Asp Ile Trp Lys Leu Phe Arg Asn Phe Lys Asn Ser Ala Gln Leu
    295                 300                 305 tgc ctg gag ctg gag gcc tgg gaa cgg ggc agg gcc gtg gac ctc cgt          1614
Cys Leu Glu Leu Glu Ala Trp Glu Arg Gly Arg Ala Val Asp Leu Arg
310                 315                 320                 325 ggc ctg ggc ttc gac cgc gcc gcc cgg cag gtc cac gag aag gcc ctg          1662
Gly Leu Gly Phe Asp Arg Ala Ala Arg Gln Val His Glu Lys Ala Leu
                330                 335                 340 ttc ctg gtg ttt ggc cgc acc aag aaa cgg gac ctg ttc ttt aat gag          1710
Phe Leu Val Phe Gly Arg Thr Lys Lys Arg Asp Leu Phe Phe Asn Glu
            345                 350                 355 att aag gcc cgc tct ggc cag gac gat aag acc gtg tat gag tac ctg          1758
Ile Lys Ala Arg Ser Gly Gln Asp Asp Lys Thr Val Tyr Glu Tyr Leu
        360                 365                 370 ttc agc cag cgg cga aaa cgg cgg gcc cca ctg gcc act cgc cag ggc          1806
Phe Ser Gln Arg Arg Lys Arg Arg Ala Pro Leu Ala Thr Arg Gln Gly
    375                 380                 385 aag cga ccc agc aag aac ctt aag gct cgc tgc agt cgg aag gca ctg          1854
Lys Arg Pro Ser Lys Asn Leu Lys Ala Arg Cys Ser Arg Lys Ala Leu
390                 395                 400                 405 cat gtc aac ttc aag gac atg ggc tgg gac gac tgg atc atc gca ccc          1902
His Val Asn Phe Lys Asp Met Gly Trp Asp Asp Trp Ile Ile Ala Pro
                410                 415                 420 ctt gag tac gag gct ttc cac tgc gag ggg ctg tgc gag ttc cca ttg          1950
Leu Glu Tyr Glu Ala Phe His Cys Glu Gly Leu Cys Glu Phe Pro Leu
            425                 430                 435 cgc tcc cac ctg gag ccc acg aat cat gca gtc atc cag acc ctg atg          1998
Arg Ser His Leu Glu Pro Thr Asn His Ala Val Ile Gln Thr Leu Met
        440                 445                 450 aac tcc atg gac ccc gag tcc aca cca ccc acc tgc tgt gtg ccc acg          2046
Asn Ser Met Asp Pro Glu Ser Thr Pro Pro Thr Cys Cys Val Pro Thr
    455                 460                 465 cgg ctg agt ccc atc agc atc ctc ttc att gac tct gcc aac aac gtg          2094
Arg Leu Ser Pro Ile Ser Ile Leu Phe Ile Asp Ser Ala Asn Asn Val
470                 475                 480                 485 gtg tat aag cag tat gag gac atg gtc gtg gag tcg tgt ggc tgc agg          2142
Val Tyr Lys Gln Tyr Glu Asp Met Val Val Glu Ser Cys Gly Cys Arg
                490                 495                 500 tagcagcact ggccctctgt cttcctgggt ggcacatccc aagagcccct tcctgcactc        2202
ctggaatcac agaggggtca ggaagctgtg gcaggagcat ctacacagct gggtgaaag         2262 gggattccaa taagcttgct cgctctctga gtgtgacttg gctaaaggc ccccttttat         2322 ccacaagttc ccctggctga ggattgctgc ccgtctgctg atgtgaccag tggcaggcac       2382
aggtccaggg agacagactc tgaatgggac tgagtcccag gaaacagtgc tttccgatga       2442
gactcagccc accatttctc ctcacctggg ccttctcagc ctctggactc tcctaagcac      2502
ctctcaggag agccacaggt gccactgcct cctcaaatca catttgtgcc tggtgacttc       2562
ctgtccctgg acagttgag aagctgactg gcaagagtg ggagagaaga ggagagggct         2622
tggatagagt tgaggagtgt gaggctgtta gactgttaga tttaaatgta tattgatgag       2682
```
ataaaaagca aaactgtgcc t                                                    2703

<210> SEQ ID NO 2
<211> LENGTH: 501
<212> TYPE: PRT
<213> ORGANISM: homo sapiens

<400> SEQUENCE: 2

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
    290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

```
Val Tyr Glu Tyr Leu Phe Ser Gln Arg Arg Lys Arg Arg Ala Pro Leu
    370             375                 380

Ala Thr Arg Gln Gly Lys Arg Pro Ser Lys Asn Leu Lys Ala Arg Cys
385             390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
450                 455                 460

Cys Cys Val Pro Thr Arg Leu Ser Pro Ile Ser Ile Leu Phe Ile Asp
465             470                 475                 480

Ser Ala Asn Asn Val Val Tyr Lys Gln Tyr Glu Asp Met Val Val Glu
                485                 490                 495

Ser Cys Gly Cys Arg
            500
```

```
<210> SEQ ID NO 3
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: human mature monomeric GDF-5

<400> SEQUENCE: 3
```

```
gca cca cta gca act cgt cag ggc aag cga ccc agc aag aac ctt aag      48
Ala Pro Leu Ala Thr Arg Gln Gly Lys Arg Pro Ser Lys Asn Leu Lys
1               5                   10                  15 gct cgc tgc agt cgg aag gca ctg cat gtc aac ttc aag gac atg ggc      96
Ala Arg Cys Ser Arg Lys Ala Leu His Val Asn Phe Lys Asp Met Gly
            20                  25                  30 tgg gac gac tgg atc atc gca ccc ctt gag tac gag gct ttc cac tgc     144
Trp Asp Asp Trp Ile Ile Ala Pro Leu Glu Tyr Glu Ala Phe His Cys
        35                  40                  45 gag ggc ctg tgc gag ttc cca ttg cgc tcc cac ctg gag ccc acg aat     192
Glu Gly Leu Cys Glu Phe Pro Leu Arg Ser His Leu Glu Pro Thr Asn
 50                  55                  60 cat gca gtc atc cag acc ctg atg aac tcc atg gac ccc gag tcc aca     240
His Ala Val Ile Gln Thr Leu Met Asn Ser Met Asp Pro Glu Ser Thr
65                  70                  75                  80 cca ccc acc gcc tgt gtg ccc acg cga ctg agt ccc atc agc atc ctc     288
Pro Pro Thr Ala Cys Val Pro Thr Arg Leu Ser Pro Ile Ser Ile Leu
                85                  90                  95 ttc att gac tct gcc aac aac gtg gtg tat aag cag tat gag gac atg     336
Phe Ile Asp Ser Ala Asn Asn Val Val Tyr Lys Gln Tyr Glu Asp Met
            100                 105                 110 gtc gtg gag tcg tgt ggc tgt agg                                     360
Val Val Glu Ser Cys Gly Cys Arg
        115                 120
```

```
<210> SEQ ID NO 4
<211> LENGTH: 120
<212> TYPE: PRT
<213> ORGANISM: Homo sapiens

<400> SEQUENCE: 4
```

```
Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
            35                  40                  45

Glu Gly Leu Cys Glu Phe Pro Leu Arg Ser His Leu Glu Pro Thr Asn
        50                  55                  60

His Ala Val Ile Gln Thr Leu Met Asn Ser Met Asp Pro Glu Ser Thr
65                  70                  75                  80

Pro Pro Thr Ala Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
            115                 120
```

<210> SEQ ID NO 5
<211> LENGTH: 102
<212> TYPE: PRT
<213> ORGANISM: Homo sapiens
<220> FEATURE:
<221> NAME/KEY: MISC_FEATURE
<223> OTHER INFORMATION: cystine-knot domain of GDF-6

<400> SEQUENCE: 5

```
Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
            35                  40                  45

Ile Ile Gln Thr Leu Met Asn Ser Met Asp Pro Gly Ser Thr Pro Pro
        50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
            85                  90                  95

Glu Ser Cys Gly Cys Arg
            100
```

<210> SEQ ID NO 6
<211> LENGTH: 102
<212> TYPE: PRT
<213> ORGANISM: Homo sapiens
<220> FEATURE:
<221> NAME/KEY: MISC_FEATURE
<223> OTHER INFORMATION: cystine-knot domain of GDF-7

<400> SEQUENCE: 6

```
Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60
```

-continued

```
Ser Cys Cys Val Pro Ala Arg Leu Ser Pro Ile Ser Ile Leu Tyr Ile
 65                  70                  75                  80

Asp Ala Ala Asn Asn Val Val Tyr Lys Gln Tyr Glu Asp Met Val Val
                 85                  90                  95

Glu Ala Cys Gly Cys Arg
                100
```